United States Patent
Russell et al.

(10) Patent No.: US 7,854,928 B2
(45) Date of Patent: *Dec. 21, 2010

(54) METHOD FOR LIMITING THE GROWTH OF CANCER CELLS USING AN ATTENUATED MEASLES VIRUS

(75) Inventors: Stephen J. Russell, Rochester, MN (US); Adele Kay Fielding, Cambridge (GB); Kah-Whye Peng, Rochester, MN (US); Deanna Grote, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,623

(22) Filed: Jan. 15, 2010

(65) Prior Publication Data

US 2010/0119548 A1    May 13, 2010

Related U.S. Application Data

(63) Continuation of application No. 12/135,721, filed on Jun. 9, 2008, now Pat. No. 7,670,598, which is a continuation of application No. 11/532,879, filed on Sep. 18, 2006, now Pat. No. 7,393,527, which is a continuation of application No. 09/668,196, filed on Sep. 22, 2000, now Pat. No. 7,118,740.

(51) Int. Cl.
| | |
|---|---|
| *A01N 63/00* | (2006.01) |
| *C12N 7/00* | (2006.01) |
| *C12N 7/04* | (2006.01) |
| *C12N 7/02* | (2006.01) |

(52) U.S. Cl. .................. 424/93.6; 424/93.1; 435/235.1; 435/236; 435/239

(58) Field of Classification Search ........................ None
See application file for complete search history.

(56) References Cited

U.S. PATENT DOCUMENTS

| | | | | |
|---|---|---|---|---|
| 5,891,454 | A | * | 4/1999 | Wu ............................. 424/423 |
| 5,985,290 | A | * | 11/1999 | Jaffee et al. ............... 424/277.1 |
| 7,118,740 | B1 | * | 10/2006 | Russell et al. ............... 424/93.6 |
| 7,393,527 | B2 | * | 7/2008 | Russell et al. ............... 424/93.6 |
| 7,670,598 | B2 | * | 3/2010 | Russell et al. ............... 424/93.6 |

OTHER PUBLICATIONS

Heinzerling et al., "Oncolytic measles virus in cutaneous T-cell lymphomas mounts antitumor immune responses in vivo and targets interferon-resistant tumor cells," Blood, 2005, 106:2287-2294.*

Feldman et al., "Measles and Rubella antibody status in previously vaccinated children with cancer," Medical and Pediatric Oncology, vol. 16 No. 5, pp. 308-311 (1988).*

Ong et al., "Oncolytic measles virus targets high CD46 expression on multiple myeloma cells ," Experimental Hematology, vol. 34 No. 6, pp. 713-720 (Jun. 2006).*

Mitus et al., "Attenuated Measles Vaccine in Children with Acute Leukemia," American Journal of Diseases of Children, vol. 103, pp. 413-418 (Mar. 1962).*

Pasquinucci G., "Possible effect of measles on leukaemia" The Lancet, vol. 1 No. 7690, p. 136 (Jan. 1971).*

Peng et al., "Systemic therapy of myeloma xenografts by an attenuated measles virus," Blood, vol. 98 No. 7, pp. 2002-2007 (Oct. 2001).*

Peng et al., "Intraperitoneal Therapy of Ovarian Cancer Using an Engineered Measles Virus," Cancer Research, vol. 62 No. 16, pp. 4656-4662 (Aug. 2002).*

Ridgway et al., "Active immunization of shildren with leukemia and other malignacies," Leukemia and Lymphoma, vol. 9 No. 3, pp. 177-192 (Feb. 1993).*

* cited by examiner

*Primary Examiner*—Zachariah Lucas
*Assistant Examiner*—Michelle Horning
(74) *Attorney, Agent, or Firm*—Fish & Richardson P.C.

(57) ABSTRACT

A method for treating cancer cells is provided comprising directly or systemically administering a therapeutically effective dose of an attenuated measles virus. In one embodiment, the therapeutically effective dose is from about $10^3$ pfus to about $10^{12}$ pfus and is delivered by direct injection into a group of cancer cells or via intravenous injection.

23 Claims, 8 Drawing Sheets

Intravenous administration of a MV-Edm led to total regression of ARH-77 tumor xenografts

SINGLE DOSE
($1 \times 10^7$ pfu/100 µl)

Intravenous administration of a MV-Edm led to total regression of ARH-77 tumor xenografts

METHOD FOR LIMITING THE GROWTH OF CANCER CELLS USING AN ATTENUATED MEASLES VIRUS

CROSS-REFERENCE TO RELATED APPLICATIONS

This application is a continuation of and claims the benefit of priority under 35 U.S.C. §119 of U.S. application Ser. No. 12/135,721 (now U.S. Pat. No. 7,670,598), filed Jun. 9, 2008; which is a continuation of U.S. application Ser. No. 11/532,879 (now U.S. Pat. No. 7,393,527), filed Sep. 18, 2006; which is a continuation of U.S. application Ser. No. 09/668,196, filed Sep. 22, 2000 (now U.S. Pat. No. 7,118,740). The disclosures of the prior applications are incorporated by reference in their entirety.

FIELD OF THE INVENTION

The invention relates to a method for limiting cancer cell growth by administering a attenuated measles virus.

BACKGROUND OF THE INVENTION

Current standard cancer therapies include surgery, chemotherapy, radiation, and autologous cell transplantation. Surgery is generally effective in the early treatment of cancer; however, metastatic growth of tumors can prevent any complete cure. Chemotherapy, which involves administration of compounds having antitumor activity, while effective in the treatment of some cancers, is often accompanied by severe side effects, including nausea and vomiting, bone marrow depression, renal damage, and central nervous system depression. Radiation therapy has also been used to target cancer cells, as cancer cells are less able to repair themselves after treatment with radiation. However, radiation cannot be used to treat many cancers because of the sensitivity of normal cells which surround cancerous tissue.

Efforts to improve the efficacy of standard cancer therapies by combining them have been moderately successful. Multi-drug combination chemotherapy regimens and high dose therapy have improved the outlook of patients with certain types of cancer, e.g., intermediate-grade histology non-Hodgkin's lymphoma (NHL), particularly when followed by autologous stem cell rescue. However, no therapeutic options have been proven to be of benefit to patients who have active disease after transplantation.

The goal of many recent research efforts has been to specifically target cancer cells with suicide or toxic genes ("therapeutic genes") and techniques to transfer therapeutic genes into tumor cells have been developed (Freeman, et al. 1996). However, to date these techniques have been hampered by the restricted range of action of the therapeutic genes as cell killing is predominantly limited to transduced cells (Paillard, 1997). This problem is exacerbated by the fact that levels of transduction with available gene delivery vectors are low, even in vitro.

Lytic viruses with tissue tropisms can have anti-cancer effects when the natural tissue targets of these viruses include cancer cells. Anecdotal accounts of regression of Hodgkin's disease and of Non-Hodgkin's Lymphoma (NHL) after natural measles virus infection have been reported in the literature (Taqi, et al., 1991; Bluming and Ziegler, 1971). A study in which another paramyxovirus, mumps, was administered to 90 patients with advanced malignancy was reported by Asada (1974). In this study, a tissue culture suspension of wild-type mumps virus, was administered by a variety of routes, mostly to patients suffering from advanced and terminal cancer. Almost half of the patients had significant, although short-lived responses in treated regions. Newcastle Disease Virus, an avian paramyxovirus has also shown promising results in preclinical studies (Lorence, et al. 1994; Lorence, et al.1988; Reichard, et al. 1992); however, humans lack any natural immunity to the virus, discouraging its widespread use in humans.

SUMMARY OF THE INVENTION

The invention provides a means to limit the growth of cancer cells simply and effectively using a form of measles virus typically found in vaccines, e.g., an attenuated measles virus. By directly administering a therapeutically effective dose of attenuated measles virus into a site of cancer cell growth (e.g., intratumorally) or by administering the virus systemically (e.g., intraveneously), the growth of cancer cells is limited.

In one embodiment of the invention, a therapeutically effective dose of attenuated measles virus is administered directly to a group of cancer cells (e.g., a tumor) by injection. In another embodiment of the invention, the therapeutically effective dose is administered directly to a group of cancer cells by implanting a source of attenuated measles virus in proximity to, or within, a group of cancer cells. In this embodiment, the source of attenuated measles virus is a formulation comprising an effective dose of attenuated measles virus and an excipient. Degradation of the excipient by bodily fluids brings the virus into contact with the tumor cells. The therapeutically effective dose can either be provided continuously to the patient or in pulsed doses.

In another embodiment of the invention, the therapeutically effective dose is administered systemically to a patient intravenously, such as by injection or through a medical access device such as a catheter.

In one embodiment according to the invention, the therapeutically effective dose is a dose of about $10^3$ to about $10^{12}$ pfu. In another embodiment of the invention, the therapeutically effective dose is greater than about $10^3$ pfu. In a further embodiment of the invention, the therapeutically effective dose is about $10^5$ pfus, $10^6$ pfus, $10^7$ pfus, or $10^8$ pfus. In one embodiment of the invention, the therapeutically effective amount of attenuated measles virus is an amount effective to cause a reduction in the number of cancer cells in a patient or regression of a tumor is a patient relative to the size of the group of cancer cells or tumor prior to administration of the virus.

In another embodiment of the invention, the therapeutically effective dose of attenuated measles virus is provided in a composition comprising attenuated measles virus, an attenuated mumps virus, and an attenuated rubella virus. In a further embodiment of the invention, the attenuated measles virus is provided in a composition comprising an attenuated rubella virus.

In one embodiment of the invention, the attenuated measles virus is genetically modified to express a marker polypeptide (e.g., β-galactosidase or Green Fluorescent Protein (GFP)) whose expression correlates with the replication of the virus. In another embodiment of the invention, the marker polypeptide is detectable in a bodily fluid obtained from the patient.

In one embodiment of the invention, the method is used to limit the growth of cancer cells which are selected from the group consisting of melanoma, carcinoma, glioma, myeloma cells, and combinations thereof. In another embodiment of the invention, the myeloma cells are lymphoma cells. In still another embodiment of the invention, the lymphoma cells are Non-Hodgkin's Lymphoma cells.

BRIEF DESCRIPTION OF THE DRAWINGS

The objects and features of the invention can be better understood with reference to the following detailed description and accompanying drawings.

FIG. 1A shows quantification of CD46 expression by flow cytometry analysis (FACS) using an anti-CD46 antibody and a secondary antibody conjugated to fluorescein isothiocyanate (FITC) demonstrating that the majority of DoHH2 and Raji cells express CD46. The shaded histograms represent cells incubated with isotype controls. The line histograms represent the fluorescent intensity of cells after incubation with anti-CD46 antibody. FIG. 1B shows replication of an attenuated measles virus according to one embodiment of the invention bearing a marker gene (MVlacZ). The open squares represent the titer of MVlacZ on Raji cells. The closed triangles represent the titer of Mvlac Z cells on DoHH2 cells. FIG. 1C shows that infection of Raji cells by MV-Edm results in a characteristic cytopathic effect with the formation of multinucleated cells in suspension culture. Non-infected Raji cells are shown in comparison with MV-Edm-infected cells four days after infection. Giant multinucleated cells are seen after infection with attenuated measles virus.

FIG. 2A shows percentage change in tumor volume of DoHH2 tumors treated with $10^5$ pfu MVlacZ. FIG. 2B shows percentage change in tumor volume of Raji tumors treated with $10^6$ pfu MVlacZ. FIG. 2C shows percentage change in tumor volume of Raji tumors, treated with $4 \times 10^7$ pfu MVlacZ. FIG. 2D shows a comparison of responses to small ($<04.cm^3$) or large ($>0.4 \times m^3$) tumors treated with attenuated measles virus.

FIG. 3A shows hematoxylin and eosin staining of a section of a Raji tumor cell showing multiple multinucleated syncytia. FIGS. 3B and C show consecutive tissue sections stained with hematoxylin and eosin and with an anti-measles virus anti-H protein antibody. Anti-H staining is co-incident with the measles virus-induced cytopathic effect. FIGS. 3D and E show consecutive tissue sections stained with hematoxylin and eosin and subjected to in situ hybridization to detect MV mRNA. FIGS. 3F and G show macroscopic and microscopic β-galactosidase expression in tumor and tumor sections (as measured by X-gal staining), respectively, which were injected with MVlacZ. The injected tumor shows considerable X-gal staining macroscopically compared to a control tumor which does not stain. Microscopically, β-galactosidase expression is co-incident with measles virus-induced syncytia. FIG. 3G shows β-galactosidase expression in Vero cells 24 hours after co-culture with a small tumor section from a mouse injected with MVlacZ. Large X-gal stained syncytia can be seen, due to replicating MVlacZ recovered from the tumor. FIG. 3H shows hematoxylin and eosin staining of the same tissue.

FIG. 4A shows a lack of N mRNA expression in a tumor injected with UV-inactivated attenuated measles virus. FIG. 4B shows expression of N mRNA in a tumor injected with MV-Edm in syncytia. FIG. 4C is a higher magnification of the boxed area shown in FIG. 4B.

FIG. 5A shows the effects of a single dose of $10^7$ pfu (closed circle) or UV-inactivated MV-Edm injected into the tail vein of SCID mice (n=4 mice per treatment group). FIG. 5B shows the effects of multiple doses at $10^7$ pfu/dose (n=6 mice per treatment group).

DETAILED DESCRIPTION

Figure 1:
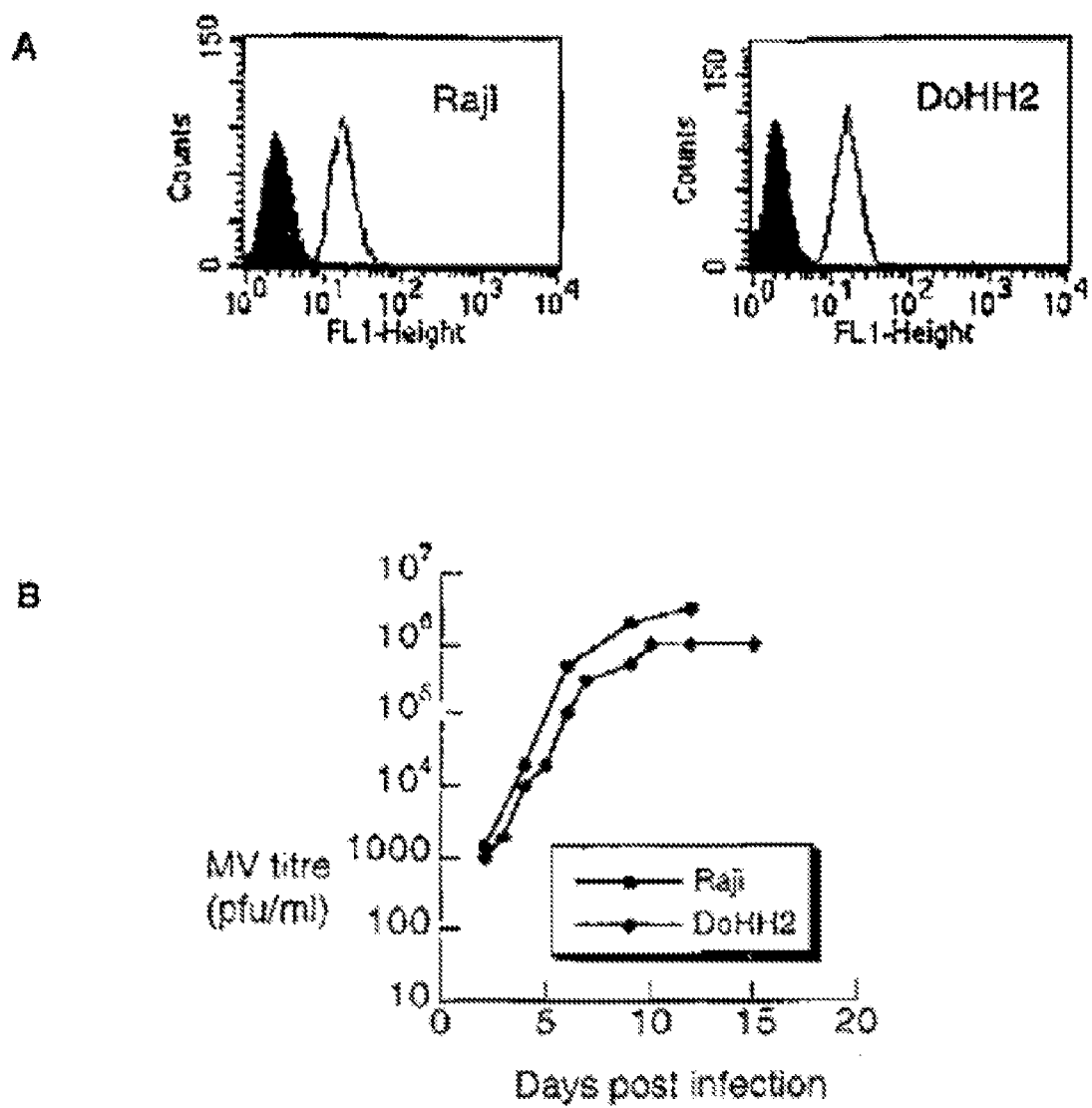
FIGS. 1A-C show lytic infection of DoHH2 and Raji lymphoma cell lines after delivery of effective doses of attenuated measles virus according to one embodiment of the invention.

Measles virus is a negative strand RNA virus whose genome encodes six protein products, the N (nucleocapsid), P (polymerase cofactor phosphoprotein), M (matrix), F (fusion), H (hemaglutinin) and L (large RNA polymerase) proteins. The H protein is a surface glycoprotein which mediates measles virus attachment to its receptor, CD46 (Dorig, et al., Cell 75: 295-305, 1993). The F protein is responsible for cell-cell fusion after viral attachment has taken place. Measles virus has a natural tropism for lymphoid cells and, in particular, cancerous lymphoid cells.

The tumor selectivity of the virus is due to intracellular restrictions to the life cycle of the virus that is strongly inhibitory to virus propagation in nontransformed cells, but which are overriden by cellular factors present in neoplastic cells (Robbins, et al., Virology 106: 317-326, 1980; Robbins, Intervirology 32: 204-208, 1991). Measles infectivity of lymphoid cells causes a very characteristic cytopathic effect. Multinucleated giant cells develop during measles virus replication in lymph nodes as a result of gross cell-cell fusion (Warthin, Arch. Pathol. 11: 864-874, 1931). In tissue culture, infection with measles virus can cause fusion of a whole monolayer of cells. The F and H antigens are found on the surface of infected cells. Thus, cells which are infected by measles virus and whose membranes express F and H proteins become highly fusogenic and can cause fusion not only of other infected cells but also of neighboring cells which are not infected (Norrby and Oxman, "Measles Virus." In *Virology*, 1990, B. N. Fields, et al., eds. New York, Raven Press, Ltd., pp 1013-1044). The expression of viral antigens on the surface of a tumor cell can also mediate a tumor specific immune response.

The method according to the invention comprises administering an effective dose of an attenuated measles virus directly at a site of cancer cell growth (e.g., by intratumoral injection), or systemically (e.g., through intravenous injection), to limit and/or reduce the amount of cancer cells in a patient.

DEFINITIONS

In order to more clearly and concisely describe and point out the subject matter of the claimed invention, the following definitions are provided for specific terms which are used in the following written description and the appended claims.

As defined herein, the term "attenuated" means a virus which is immunologically related to the wild type measles virus (i.e., the virulent virus) but which is not itself pathogenic and does not produce a "classical measles disease," and is not a wild type virus. An attenuated measles virus is replication-competent, in that it is capable of infecting and replicating in a host cell without additional viral functions supplied by, for example, a helper virus or a plasmid expression construct encoding such additional functions.

As used herein, the terms "wild-type" or "wild-type virus" refer to the characteristics of a measles virus as it is found in nature which is pathogenic.

As used herein, a "pathogenic measles virus" is one which produces classical measles disease.

As defined herein, "classical measles disease" is a syndrome comprising fever, coryza, cough, conjunctivitis, followed by the appearance of a maculopaular rash (Koplik spots) which occurs upon infection with a wild type measles virus in an individual who is not immune to the virus.

As used herein, the term "patient" refers to an organism to which viruses of the invention can be administered. Preferably, a patient is a mammal, e.g., a human, primate or a rodent.

As used herein, the term "biological fluid" refers to any extracellular bodily fluid, including but not limited to blood, urine, saliva, interstitial fluid, lymph, and cerebrospinal fluid.

As used herein, the term "administering directly to a group of cancer cells" or "administering directly to a tumor" refers to injecting or implanting a source of attenuated measles virus either in proximity to (within 1-2 cm of), or within a tumor.

As used herein, the term "administering systemically" refers to exposure of the cells of an organism to an attenuated measles virus via the circulatory system of the patient, such as by intravenous injection or the use of a medical access device, such as a catheter.

As defined herein, "plaque forming units" or "pfus" refers to areas of destroyed cells in a cell culture infected with a virus.

As defined herein, "primary isolation of measles virus" refers to isolation and culture of a measles virus from an infected patient in order to develop an attenuated strain.

As used herein, the term "recombinant virus" or "modified virus" refers to a virus or viral polypeptide which is altered by genetic engineering, by modification or manipulation of the genetic material encoding that polypeptide, or found in the virus such that it is not identical to the naturally occurring virus or polypeptide.

As used herein, the term "marker gene" refers to a gene encoding a detectable polypeptide not encoded by a wild type measles virus. A "marker polypeptide" is the polypeptide encoded by a marker gene.

As used herein, the term "detectable" refers to a property of a polypeptide that allows one to determine the presence and/or amount of the polypeptide in a biological sample. The meaning of the term "detectable" is intended to encompasses detection of activities, for example, enzyme activity or fluorescence activity possessed by the polypeptide, in addition to detection of the polypeptide by other means, for example, immunoassay or mass spectroscopy.

As used herein, "measles virus growth" refers to growth or replication of a measles virus measured by viral propagation after successive rounds of infection and replication occurring in a host organism, as measured by virus titer, or by detection of a marker polypeptide, or as measured by a reduction in tumor size.

As used herein, "reduction in size in a group of cancer cells" or "reduction in size of a tumor" refers to any decrease in the size of a group of cancer cells or a tumor following administration of an attenuated measles virus relative to the size of the group of cancer cells or tumor prior to administration of the virus. A group of cancer cells or tumor may be considered to be reduced in size or regressed if it is at least about 10% smaller, 25%, 50%, up to 100%, or having no cancer cells or tumor remaining Size is measured either directly or in vivo (i.e., by measurement of the group of cancer cells or a tumor which is directly accessible to physical measurement, such as by calipers) or by examination of the size of an image of the tumor produced, for example, by X-ray or magnetic resonance imaging or by computerized tomography, or from the assessment of other optical data (e.g., spectral data).

As defined herein, "reduction in number of cancer cells" refers at least a 10% reduction in the number of cancer cells. For a tumor, reduction in number can be measured as a reduction in size or weight of a tumor, or a reduction in the amount of a tumor specific antigen of at least 10%. For a group of cancer cells, such as a group of leukemia cells, a reduction in number can be determined by measuring the absolute number of leukemia cells in the circulation of a patient, or a reduction in the amount of a cancer cell-specific antigen of at least 10%.

As defined herein, "regression of a group of cancer cells" or "regression of a tumor" refers to a decrease in the size of a group of cancer cells/tumor as described above, and/or as a decrease in the levels of a cancer cell antigen in the patient.

As defined herein, "limiting the growth of a group of cancer cells" or "limiting the growth of a tumor" refers to decreasing the rate of growth of the cancer cells/tumor. This is measurable as an absence of any detectable change in size or weight of the cancer cells/tumor or a decrease in the rate of increase in the size of a group of cancer cells or a tumor.

As used herein, the term "tumor" is a group of cancer cells which grows at an anatomical site outside of the blood stream and requires the formation of requires the formation of small blood vessels and capillaries to supply nutrients. to the growing tumor mass.

As used herein, the term "selecting syncytia" refers to the process of physically isolating or harvesting syncytia from a monolayer culture infected with an attenuated measles virus in order to further propagate the particular form of the virus contained within a particular syncytium.

As used herein, the term "expanding" refers to the process whereby a particular virus is propagated in host cells in order to increase the available number of copies of that particular virus, preferably by at least 2-fold, more preferably by 5-10-fold, or even by as much as 50-100-fold relative to unexpanded cells.

As used herein, the term "cancer specific marker" or "tumor specific marker" is an antigen which is preferentially or exclusively expressed on cancerous cells, and is not found, or is found in lower amounts in non-cancer cells.

Producing Attenuated Vaccine Strains of Measles.

In one embodiment of the invention, an attenuated strain of virus is grown in culture to provide an effective dose which will limit and/or cause regression of a group of cancer cells such as a tumor. Attenuated strains of viruses are obtained by serial passage of the virus in cell culture (e.g., in non-human cells), until a virus is identified which immunogenic but not pathogenic. While wild type virus will cause fatal infection in marmosets, vaccine strains do not. In humans, infection with wild type viral strains is not generally fatal but is associated with classic measles disease. Classic measles disease includes a latent period of 10-14 days, followed by a syndrome of fever, coryza, cough, and conjunctivitis, followed by the appearance of a maculopapular rash and Koplik's spots (small, red, irregularly shaped spots with blue-white centers found inside the mouth). The onset of the rash coincides with the appearance of an immune response and the initiation of virus clearance. In contrast, individuals receiving an attenuated measles virus vaccine do not display classical measles symptoms. Attenuation is associated with decreased viral replication (as measured in vivo by inability to cause measles in monkeys), diminished viremia, and failure to induce cytopathological effects in tissues (e.g., cell-cell fusion, multi-nucleated cells). However, these biological changes have not been mapped to any single genetic change in the virus genome.

In a preferred embodiment of the invention, an attenuated strain of measles virus which has been clinically tested as a vaccine for measles infection is used to provide an effective dose which will limit and/or cause regression of a group of cancer cells, such as a tumor. The Moraten attenuated form of the virus has been used world-wide as a vaccine and has an excellent safety record (Hilleman, et al., J. Am. Med. Assoc. 206: 587-590, 1968). Accordingly, in one embodiment of the invention, the Moraten strain is used to provide an effective dose. The Moraten vaccine is commercially available from Merck® and is provided lyophilized in a vial which when reconstituted to 0.5 ml comprises $10^3$ pfu/ml. A vaccine against the Moraten Berna strain is available from the Swiss Serum Vaccine Institute Berne.

In a further embodiment of the invention, the Edmonston-B vaccine strain of measles virus is used (MV-Edm) (Enders and Peebles, Proc. Soc. Exp. Biol. Med. 86: 277-286, 1954). MV-Edm grows efficiently in tumor cells but its growth is severely restricted in primary cultures of human peripheral blood mononuclear cells, normal dermal fibroblasts, and vascular smooth muscle cells. A form of the Enders attenuated Edmonston strain is available commercially from Merck (Attenuvax®). Other attenuated measles virus strains are also encompassed within the scope of the invention, such as Leningrad-16, and Moscow-5 strains (Sinitsyna, et al., Res. Virol. 141(5): 517-31, 1990), Schwarz strain (Fourrier, et al., Pediatrie 24(1): 97-8, 1969), 9301B strain (Takeda, et al. J. VIROL. 72/11: 8690-8696), the AIK-C strain (Takehara, et al., Virus Res 26 (2): 167-75, 1992 November), and those described in Schneider-Shaulies, et al., PNAS 92(2): 3943-7, 1995, the entireties of which are incorporated by reference herein.

In a further embodiment of the invention, the measles virus is provided in a composition comprising a mixture of attenuated oncolytic viruses. In one embodiment, the mumps measles and rubella vaccine (MMR) is used. The MMR vaccine was introduced into the United States in 1972 and into the United Kingdom in 1998. Commercially available preparations of the MMR vaccine is obtainable from Merck, Pasterur Merieux Connaught, or SmithKline Beecham, and also contain the Moraten strain of attenuated measles virus at a minimum titer of $10^3$ PFU/ml. In still a further embodiment of the invention, the measles virus is provided in a composition comprising Edmonston Zagreb measles strain (an attenuated strain obtained from the Edmonston-enders stain) and the Wistar RA 27/3 strain of rubella (Swiss Serum Vaccine Institute Berne). It should be apparent to those of skill in the art that any clinically tested measles vaccine is acceptable for use in the invention, and is encompassed within the scope of the invention.

In one embodiment of the invention, an effective dose of an attenuated measles virus is produced by infecting a primary cell or a continuous cell line with a starting innoculum of an stock comprising an attenuated Moraten strain of measles virus (or an innoculum of an MMR stock) or the MV-Edm strain or any of the other strains described above and expanding the virus after serial passage. Cells or cell lines encompassed within the scope of the invention include, but are not limited to, monkey kidney or testes cells or monkey cell lines (e.g., Vero, KB, CV-1, BSC-1, and the like). Viral replication in cells is observed as cell-cell fusion and syncytia formation.

The attenuated measles virus is expanded until a desired dose concentration is obtained in standard cell culture media (e.g., DMEM or RPMI-1640 supplemented with 5-10% fetal bovine seurm at 37° C. in 5% $CO_2$). In one embodiment of the invention, the therapeutically effective dose concentration is about $10^3$ to $10^{12}$ pfu. In another embodiment of the invention, the concentration is about $10^5$ to $10^8$ pfu. Viral titer is assayed by inoculating cells (e.g., Vero cells) in culture dishes (e.g., such as 35 mm dishes). After 2-3 hours of viral adsorption, the inoculum is removed and cells are overlaid with a mixture of cell culture medium and agarose or methylcellulose (e.g., 2 ml DMEM containing 5% FCS and 1% Sea-Plaque agarose). After about 3 to about 5 days, cultures are fixed with 1 ml of 10% trifluoroacetic acid for about 1 hour, then UV cross-linked for 30 minutes. After removal of the agarose overlay, cell monolayers are stained with crystal violet and plaques are counted to determine viral titer. Virus is harvested from cell syncytia by scraping cells from the dishes, subjecting them to freeze/thawing (e.g., approximately two rounds), and centrifuging. The cleared supernatants represent "plaque purified" virus.

Viral stocks are produced by infection of cell monolayers (e.g., adsorption for about 1.5 hours at 37° C.), followed by scraping of infected cells into a suitable medium (e.g., Opti-MEM, Gibco-BRL) and freeze/thaw lysis (e.g., 2 rounds). Viral stocks are aliquoted, frozen and stored at –70° C.-80° C. and can be stored at concentrations higher than the therapeutically effective dose. In one embodiment of the invention, the viral stock is stored in a stabilizing solution. Stabilizing solutions are known in the art and include, for example, sugars (e.g., trehalose, dextrose, glucose), amino acids, glycerol, gelatin, monosodium glutamate, $Ca^{2+}$ and $Mg^{2+}$. Suitable stabilizing solutions are described in U.S. Pat. No. 4,985,244, and U.S. Pat. No. 4,500,512, the entireties of which are incorporated by reference herein.

In another embodiment of the invention, an attenuated measles virus strain is generated from a primary measles strain. In this embodiment, a primary measles virus is isolated by inoculating a cell line with peripheral blood leukocytes or respiratory secretions from a patient. Suitable cells and cell lines include, but are not limited to, primary human cells (e.g., blood, lung, conjunctiva, kidney, intestine, amnion, skin, muscle, thymic stroma, foreskin, and uterus), human cell lines (e.g., Wi-38, MRC-5, Hep-2, HeLa, A549), primary monkey cells (e.g., kidneys, and testes), and monkey cell lines (e.g., Vero, KB, CV-1, and BSC-1), and the Epstein-Barr virus-transformed marmoset B lymphocyte cell line (B95-8).

Cells are passaged until propagation of wild-type virus and production of cytopathic effects can be detected in tissue culture, such as cell-cell fusion and syncytia formation. In one embodiment of the invention, viral stocks are prepared using a low multiplicity of infection to avoid the accumulation of defective particles. Plaques become visible after about 3 to five days of culture, and the virus is allowed to continue to replicate until a desired concentration is reached. Viral titers are determined as described above.

Once a primary measles virus is isolated in culture, it serially passaged in a non-human cell line. The Edmonston strain was produced by Enders as a result of successive series of passages through human kidney tissue culture, human amnion tissue culture, embryonated eggs and chick embryo tissue culture. Clones of measles virus obtained in the last culture passage and suspensions of viruses are obtained and purified by centrifugation or filtration to completely remove any culture cells. Attenuated virus suspensions with desired properties are selected (e.g., high infectivity, high immunogenicity, and low pathogenicity).

The infectivity of an attenuated virus suspension is determined by determining a dilution of virus that produces cytopathic effects (cell-cell fusion and syncytia formation observed microscopically) in at least 50% of cultured cells (e.g., 5 out of 10 test tubes comprising 5 ml cultures of Vero cell sheets). In one embodiment of the invention, an attenuated virus suspension is selected which causes cytopathic effects in 50% of infected Vero cells at least a $10^3$-fold dilution (i.e., having a $TCID_{50}$ of 3) (see "Review of Medical Microbiology", 13th ed., pp. 344-345, Lange Medical Publications, 1976).

The immunogenicity of an attenuated virus suspension is determined by evaluating seroconversion in monkeys after injection with the virus. Seroconversion is measured by determining the levels of antibody before and after immunization (% of increase in the amount of a specific antibody). In one embodiment of the invention, an attenuated vaccine produces about 70% to 100% seroconversion approximately 2 months after injection.

Low pathogenicity and decreased replication efficiency is determined by evaluating the appearance of classic measles symptoms in monkeys (see, e.g., Kobune, et al., Lab Anim. Sci. 46 (3): 315-20, 1996). In one embodiment of the invention, an attenuated measles virus suspension is selected which does not produce classical measles in monkeys (e.g., within a month). Although measles can be viewed as a continuum of symptoms (fever, coryza, cough, and conjunctivitis, followed by the appearance of a rash and Koplik's spots), symptoms that are generally the same as the adverse effects observed with the Attenuvax® vaccine are not considered "measles," in this embodiment of the experiment. Thus symptoms such as moderate to high fever lasting 1-2 days, a rash lasting 1-2 days, cough and rhinitis, and/or erythma multiforme (skin rash) would not cause a monkey to be identified as having measles. In one embodiment, the classification of a monkey as having measles is dependent on the appearance of Koplik's spots.

In additional embodiments, properties such as thermosensitivity can be selected (see, e.g., U.S. Pat. No. 4,211,843, U.S. Pat. No. 4,071,618 and U.S. Pat. No. 3,133,861, the entirety of which is incorporated by reference herein). Non-human cell lines according to the invention include, but are not limited to chick embryos, quail embryos, duck embryos, and dog and bovine kidney cells.

In still a further embodiment of the invention, recombinant measles viruses comprising genetic modifications are derived from wild type measles virus to generate attenuated viruses, e.g., viruses having high immunogenicity (as measured by 70-100% seroconversion) and no pathogenicity (e.g., not producing classical measles symptoms, as discussed above). In one embodiment of the invention, genetic modifications are introduced through random mutagenesis of a plasmid comprising the sequence of a wild type measles virus. Sequences of wild type isolates are disclosed in U.S. Pat. No. 5,578,448, the entirety of which is enclosed herein by reference.

In another embodiment of the invention, particular cistrons in the measles virus genome are targeted to modify genes whose expression is associated with attenuation (Schneider-Shaulies, et al. PNAS 92(2): 3943-7, 1995; Takeda, et al. J. Virol. 1998 72/11 (8690-8696)). Thus, in one embodiment of the invention, a recombinant measles virus strain is generated comprising a single point mutation or multiple non-contiguous point mutations in any of an H protein, a V protein, a C protein, and combinations thereof. In still a further embodiment of the invention, natural variants of the wild type or attenuated measles viruses are identified (e.g., such as from cultures of virus from infected patients) which have at least one point mutation in their genome.

Methods of Treating Cancer Using Attenuated Measles Vaccine:

Dosage, Administration and Pharmaceutical Formulation

Attenuated measles virus when used to immunize against measles is typically injected in a single $10^3$ dose subcutaneously or intramuscularly. The MMR vaccine is typically administered twice at the same dose, and is also administered subcutaneously or intramuscularly.

In one embodiment according to the invention, attenuated measles virus is injected either directly into a group of cancer cells (e.g., a tumor) or is delivered intravenously to cancer cells. Types of cancer cells susceptible to treatment with attenuated measles or MMR include neuronal cells, glial cells, myelomonocytic cells, and the like. Types of cancer treatable by the method according to the invention, include, but are not limited to, myeloma, melanoma, glioma, and breast carcinoma. In one embodiment of the invention, the attenuated measles virus is used to limit or cause regression of lymphomas. In still a further embodiment of the invention, the attenuated measles virus is used to limit or cause the regression of cancer cells in a patient with Non-Hodgkin's Lymphoma. In one embodiment of the invention, direct delivery into one type of cancer cells (e.g., a lymphoma) is used to reduce or limit the growth of a different type of cancer (e.g., a carcinoma).

In one embodiment, the attenuated measles virus is administered to the patient in a biologically compatible solution or a pharmaceutically acceptable delivery vehicle, by administration either directly into a group of cancer cells (e.g., intratumorally) or systemically (e.g., intravenously). Suitable pharmaceutical formulations, in part, depend upon the use or the route of entry, for example transdermal, or by injection. Such forms should not prevent the composition or formulation from reaching a target cell (i.e., a cell to which the virus is desired to be delivered to) or exerting its effect. For example, pharmacological compositions injected into the blood stream should be soluble.

While dosages administered will vary from patient to patient (e.g., depending upon the size of a tumor), a "therapeutically effective dose" will be determined by setting as a lower limit, the concentration of virus proven to be safe as a vaccine (e.g., $10^3$ pfu) and escalating to higher doses of up to $10^{12}$ pfu, while monitoring for a reduction in cancer cell growth along with the presence of any deleterious side effects. A therapeutically effective dose will be that dose which provides at least a 10% reduction in the number of cancer cells or in tumor size and can be detected in the circulation by detection of an antigen and correlation of the antigen to the presence of the cancer cell. Escalating dose studies are routine in the art (see, e.g., Nies and Spielberg, "Principles of Therapeutics," In Goodman & Gilman's *The Pharmacological Basis of Therapeutics*, eds. Hardman, et al., McGraw-Hill, NY, 1996, pp 43-62).

In preferred embodiments of the invention, a composition comprising an attenuated measles virus is delivered in a therapeutically effective dose in the range of from about $10^3$ pfu to about $10^{12}$ pfu. In one embodiment of the invention, the dose range is $10^5$ to $10^7$ pfu. In some embodiments, the therapeutically effective dose is provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same, or further modified virus) can be administered by the same route as initially used or by another route. A therapeutically effective dose can be delivered in several discrete doses (e.g., days or weeks apart) and in one embodiment of the invention, one to about twelve doses are provided. Alternatively, a therapeutically effective dose of attenuated measles virus is delivered by a sustained release formulation.

Devices for providing sustained release formulations are known in the art, and generally include a polymeric excipient (e.g., a swellable or non-swellable gel, or collagen) which is implanted at a site of drug delivery, and from which drug is gradually dispensed over time as a continuous or pulsed dose (see, e.g., U.S. Pat. No. 5,980,508, U.S. Pat. No. 5,001,692, and U.S. Pat. No. 5,137,727, the entireties of which are incorporated by reference herein). In one embodiment of the invention, a therapeutically effective dose of attenuated measles virus is provided within a polymeric excipient and the excipient/virus composition is implanted at a site of cancer cells (e.g., in proximity to, or within a tumor). In this embodiment, the action of body fluids gradually dissolves the excipient and continuously releases the effective dose of measles virus over a period of time. In another embodiment, a sustained release device which comprises a series of alternating active and spacer layers is implanted at a site of cancer cells. In this embodiment, each active layer of the device comprises a dose of attenuated virus embedded in excipient, while each spacer layer comprises only excipient or low concentrations of virus (i.e., lower than the effective dose). As each successive layer of the device dissolves, pulsed doses of attenuated measles virus are delivered. The size/formulation of the spacer layers determines the time interval between doses and is optimized according to the therapeutic regimen being used.

Direct administration can be performed according to any of a number of methods routinely practiced in the art. In one embodiment of the invention, a tumor which is palpable through the skin (e.g., such as a lymphoma) is injected directly with attenuated measles virus through the skin (e.g., using ultrasound guidance). In another embodiment of the invention, direct administration occurs via a catheter line or other medical access device and is used in conjunction with an imaging system (see, e.g., U.S. Pat. No. 6,095,976; U.S. Pat. No. 6,026,316; and U.S. Pat. No. 5,713,858) to localize a group of cancer cells. In this embodiment, an implantable dosing device is placed in proximity to the group of cancer cells using a guidewire inserted into the medical access device. In still another embodiment of the invention, an effective dose is directly administered to a group of cancer cells visible in an exposed surgical field.

In another embodiment of the invention, the attenuated measles virus is delivered systemically. In one embodiment, the attenuated measles virus is delivered intravenously via injection or via an intravenous delivery device designed for administration of multiple doses of a medicament. Such devices include, but are not limited to, winged infusion needles, peripheral intravenous catheters, midline catheters, peripherally inserted central catheters (PICC), and surgically placed catheters or ports (see, e.g., U.S. Pat. No. 6,012,034). Peripheral intravenous catheters and winged infusion needles are inserted into a small peripheral vein in the lower arms and hands. With peripheral intravenous catheters, the entry site must be changed every few days or as required. Peripheral intravenous catheters are often used for short-term therapy and can also be used until a long-term access device can be inserted.

The course of therapy can be monitored by evaluating changes in clinical symptoms (known in the art for each particular type of cancer) or by direct monitoring of the size of a group of cancer cells or tumor. Viral therapy using an attenuated measles viruses is effective if tumor size and/or clinical symptoms are reduced following administration of virus. In one embodiment of the invention, the method effects at least a 10% reduction in the size of a group of cancer cells within a given time period, such as one to four weeks. In further embodiments of the invention, the method effects reductions of 25%, 50% 75% and up to about 100%.

Reduction in size in a group of cancer cells or tumor cells is measured, as discussed above, either directly, using calipers, or by using imaging techniques (e.g., X-ray, magnetic resonance imaging, or computerized tomography) or from the assessment of non-imaging optical data (e.g., spectral data). Reduction in the levels of a cancer specific antigen in a patient can alternatively, or additionally, be monitored. Cancer specific antigens include, but are not limited to carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4. In this embodiment, an effective dose of attenuated measles virus is that which produces a reduction in levels of cancer specific antigens of at least 10%.

In a further embodiment of the invention, cytotoxic lymphocyte (CTL) responses to the tumor are measured to identify an increased tumor specific immune response after treatment. In this embodiment, a patient's T-cells are isolated and frozen both prior to administration of the attenuated measles virus and after treatment, when a group of cancer cells/tumor is biopsied. CTL responses are measured using methods routinely used in the art (e.g., U.S. Pat. No. 6,083,751 and Herin et al., Int. J. Cancer, 39:390-396 (1987)). In still a further embodiment of the invention, a biopsy of a patient's cancer cells/tumor before and after injection is monitored to determine alterations in the histology of the cancer cells/tumor such as cell-cell fusion and lysis. In this embodiment, an effective dose is one which causes at least one cell to have >20 nuclei. Any, or all, of these assays may be used to monitor the effectiveness of an attenuated measles vaccine.

In preferred embodiments of the invention, the vaccines are administered to patients who are not immunocompromised as determined by assessing immunoglobulin levels, absolute lymphocyte count, CD4:CD8 ratio and DTH and who also have a pre-existing measles virus immunity. Throughout the treatment, patients are monitored for the existence of any classical measles symptoms, and dosages are titrated accordingly, to minimize the presence of such symptoms.

Producing Attenuated Measles Virus Expressing Marker Polypeptides

Therapeutic effects of an attenuated measles virus can be correlated with levels of attenuated measles virus replication by measuring levels of viral protein and/or nucleic acids in cancer cells. However, a method which does not require the repeated isolation of tumor cells is preferred. In one embodiment of the invention, an attenuated strain of measles virus is genetically modified to provide a convenient means to measure viral replication. In this embodiment of the invention, a recombinant attenuated virus is modified by the insertion of a marker gene encoding a marker polypeptide within the viral genome.

In one embodiment of the invention, a marker gene encoding a marker polypeptide is inserted into a marker plasmid comprising the sequence of an attenuated measles virus genome but lacking cistrons encoding the membrane glycoproteins or the viral polymerase using standard cloning techniques well known in the art. Recombinant attenuated measles viruses are isolated (i.e., rescued) by co-transfecting a helper cell line with the mutagenized plasmid and a plasmid expressing the measles virus L polymerase. The L protein is expressed transiently, rather than stably, since high levels of L expression can impair the rescue of virus, while transient expression allows titration of the L protein as needed (Radecke, et al., 1995, the entirety of which is incorporated herein by reference). The helper cell line comprises cells (e.g., human embryonic kidney cells) stably expressing the wild type MV N and P measles proteins, i.e., providing the remaining functions of necessary for the virus to infect and replicate. The construction of an exemplary helper cell line (e.g., 293-3-6 cells) is described in Radecke, et al., 1995, supra.

After a suitable period of time following transfection (e.g., two days), cells are expanded into larger culture dishes (e.g., 90 mm dishes) and cultured (e.g., for another two days) before scraping and adsorption to cell monolayers. Infected Vero cells are monitored for syncytia formation, and syncytia are picked and propagated further, until a desired concentration is obtained (e.g., $10^3$-$10^8$ pfu). Viral stocks are produced as described above.

Detection of Marker Polypeptides in a Patient

Detection of the marker polypeptide in a biological fluid sample obtained from a patient is correlated with the expression of viral proteins, and therefore with replication of the virus. The presence of the marker polypeptide in the biological fluid sample can be determined by any qualitative or quantitative method known in the art. Immunologic assays such as ELISA or radioimmunoassay provide specific, sensitive, and quantitative results, and are suitable for automation. Chromatographic methods such as HPLC, optionally combined with mass spectrometry, can also be used. Other analytic methods, include, but are not limited to, the use of specific color reagents, thin layer chromatography, electrophoresis, spectroscopy, nuclear magnetic resonance, and the like.

While it is generally preferred that the marker polypeptide itself be non-functional, i.e., that it not possess any significant biological activity which might interfere with the patient's physiology or therapy, in one embodiment, the marker polypeptide possesses an enzyme activity which can itself be quantified and used as the means of detecting the marker in a biological fluid sample.

Any number of marker polypeptides can be used so long as they are expressed at a level which is directly proportional with the level of viral replication in vivo. In one embodiment of the invention, the marker protein is a non-naturally occurring peptide (e.g., β-galactosidase, Green Fluorescent Protein or GFB). In another embodiment of the invention; a natural marker polypeptide is used. When natural polypeptides are used, the background level of the polypeptide is determined prior to administration of the attenuated measles virus and is simply subtracted from the value determined after infection. Suitable marker polypeptides are disclosed in U.S. Provisional Application Ser. No. 60/155,873, the entirety of which is incorporated herein by reference.

The level of expression of the virus, and hence the amount of viral replication, can be correlated with the concentration of the marker polypeptide in a biological fluid sample. Determination of the relationship between an amount of marker polypeptide in a given biological fluid sample and the actual tissue level of an attenuated measles virus protein is performed by quantifying both the marker polypeptide and a viral protein product itself. In one embodiment of the invention, an infected tissue making the viral protein is extracted and the product is measured over a sufficient time period using HPLC, ELISA, a radioimmunoassay, a Western blot, or another suitable method. This permits a correlation to be made between the level of viral protein being expressed and the level of marker polypeptide detectable in the biological fluid (e.g., blood).

In one embodiment of the invention, the effective dose of attenuated measles virus is monitored by measuring the level of marker polypeptide in a patient's bodily fluid. In one embodiment of the invention, levels of marker protein are titrated against known effective doses which result in a desired therapeutic endpoint (e.g., 10% regression or reduction in the size of cancer cells or tumors or a 10% reduction in the level of a cancer specific antigen). In another embodiment, patients are monitored for levels of marker polypeptide associated with the desired therapeutic endpoint, and additional doses of attenuated measles virus are provided, as needed, to reach a level of marker polypeptide associated with the desired therapeutic endpoint.

Example 1

Using Attenuated Measles Virus to Limit Cancer Growth in a Non-Hodgkin's Lymphoma Model Performing the method according to the invention caused regression of an established tumor xenograft in SCID mouse models of B cell lymphoma. In one embodiment, two well-established lymphoma models, Raji and DoHH2 cells were used to represent high grade and low grade models, respectively, of Non-Hodgkin's Lymphoma. The Raji cell line was derived from a patient with Burkitt's lymphoma and is Epstein Bar Virus (EBV) positive. The DoHH2 cell line is EBV negative and derived from a patient with follicular lymphoma. Lymphoma xenografts were established by injecting $10^7$ cells subcutaneously in the flank region of SCID mice.

Measles Virus Replicates Lytically in Dohh2 and Raji Cells

Non-modified Edmonston-B measles virus and measles virus genetically modified by the addition of a β-galactosidase reporter gene (MVlacZ) were generated by innoculation into Vero cells. MVlacZ reaches a maximum titer of about one log less than MV-Ed (21). Stocks of MV-Ed with a titer of $4×10^7$ pfu/ml and MvlacZ stocks with a tire of $1×10^6$ pfu/ml were obtained and stored at −70° C. in aliquots, ready for injection. The expression of CD46, the receptor for MV-Ed was quantified on the lymphoma cell lines to be used. FIGS. 1A-C show that both cell lines express CD46 to a similar extent. After inoculation with MV at a multiplicity of infection (MOI) of 0.001, the Raji and DoHH2 cells were lytically infected by both MV-Ed and MVlacZ. FIG. 1B shows that both cell lines can be infected by MVlacZ in suspension culture and that the titres of virus reached a maximum of $10^6$ pfu/ml in DoHH2 cells and $3×10^6$ pfu/ml (Raji). The viruses propagated more quickly and were more rapidly lytic in Raji cells. All the cells in the MVlacZ infected Raji culture were lysed after 15 days of infection, whereas the equivalent DoHH2 culture did not lyse until 25 days after infection. Considerable cytopathic effects occurred after 4-7 days of infection, with readily observable multinucleated giant cells, as shown in FIG. 1C.

Infection with Measles Virus Abolishes the Tumorigenicity of Both Dohh2 and Raji Cells.

DoHH2 and Raji cells were infected in vitro with MV-Ed. at the first appearance of mutlinucleated cells in the suspension cell culture, $10^7$ viable infected DoHH2 or Raji cells were injected subcutaneously into the flank region of each of 10 Balb/C SCID mice (Jackson Laboratories, Bar Harbour, Me.). Simultaneously, the same number of viable, non-infected cells were injected as controls. Table 1 shows that infection of cells with measles virus prevented DoHH2 tumor growth. One of 10 mice injected with attenuated measles virus infected DoHH2 cells developed tumors, whereas nine of ten mice injected with control DoHH2 cells developed tumors. Similarly, infection with the attenuated measles virus prevented Raji tumor growth. None of the 10 mice injected with MV infected Raji cells developed tumors, whereas tumors developed in all 10 mice injected with control Raji cells. Thus, infection with measles virus is able to efficiently prevent tumor growth of both DoHH2 and Raji tumors in SCID mice.

TABLE 1

Tumorigenicity of DoHH2 and Raji Cells Infected With Attenuated Measles Virus

| Mice | Number of Established Tumors Per Aliquot of Cells Injected | |
|---|---|---|
| | DoHH2 | Raji |
| Pre-infected With MV | 1/10 | 0/10 |
| | 9/10 | 10/10 |

Measles Virus Vaccine Causes Regression of Established Lymphoma Xenografts

Figure 2:
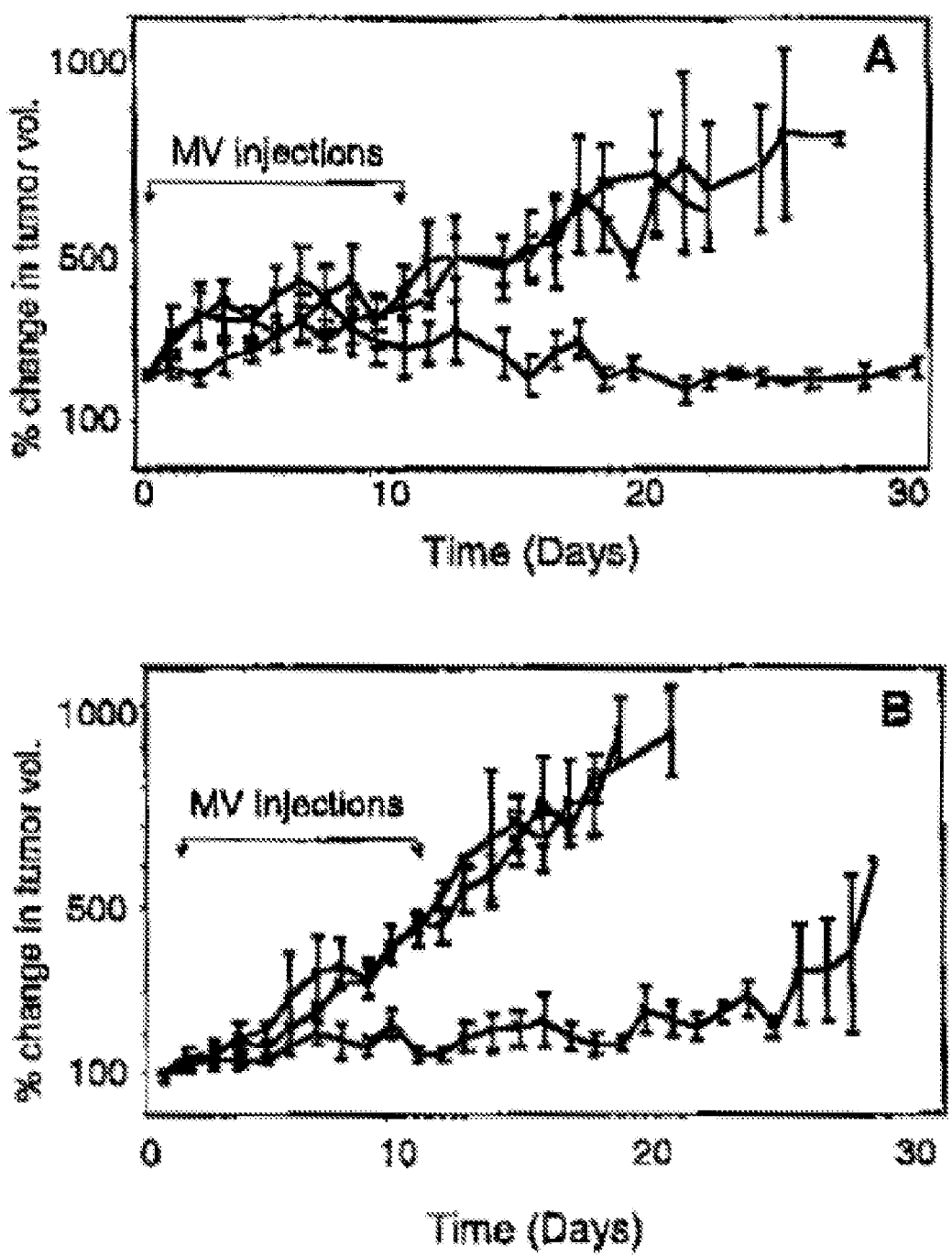
FIGS. 2A-D show the percentage change in tumor volume in tumors injected with attenuated measles virus. Mice with severe combined immunodeficiency (SCID mice) were injected daily for 10 days MVlacZ virus (closed circle) as indicated by the arrows, concurrently with UV-inactivated virus (closed triangle), and PBS (open circle). Non-injected mice (open square) served as additional controls.
Figure 2:
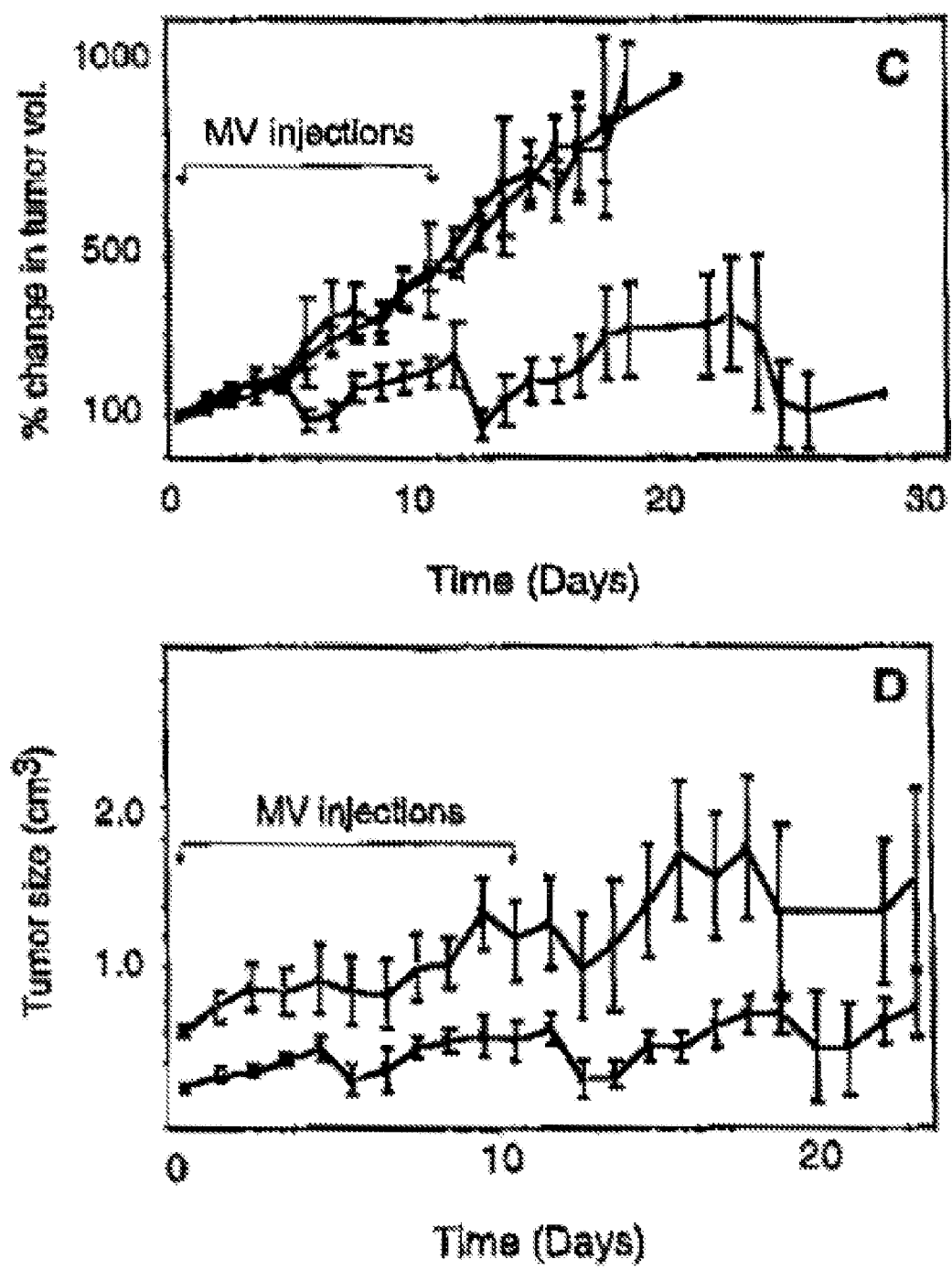

Mice bearing large established DoHH2 tumors at median volume of 0.87 cm$^3$ (range 0.23-1.63) were injected intratumorally with 10 daily doses of either $10^5$ pfu MVlacZ, inactivated MVlacZ, or PBS. Another control group was left entirely untreated. After ten injections of MVlacZ, all five of the DoHH2 tumors regressed, whereas all of the control tumors progressed. FIG. 2A shows the percentage change in tumor volume of DoHH2 tumors compared to controls. There was a significant difference in the progression rate of MVlacZ injected DoHH2 tumors compared to non-injected, PBS-injected and inactivated virus-injected controls Thus infection with MVlacZ resulted in significant tumor rejections of large, established DoHH2 tumors. Tumor regression was not observed in a single dose.

Seven mice bearing established Raji tumors were injected with $10^5$ pfu MVlacZ daily for 10 days, alongside control mice whose tumors were injected with inactivated MVlacZ or left untreated. As with the DoHH2 tumors, there was a significant difference in the rate of progression of the MVlacZ injected Raji tumors compared to that of controls injected with UV inactivated virus or the no-therapy controls (see FIG. 2B). At this dose of MV, substantial tumor regression was seen in three of seven Raji tumors. To determine if a higher doses of MV would lead to a greater response rate, eight mice bearing established Raki tumors were injected with 10 injections 4×106 pfu MV-Edm (total dose 4×10$^7$ pfu). As shown in FIG. 2C, a significant difference in rate of tumor progression as compared to controls was observed. In addition, four substantial tumor regressions were observed, with two tumors becoming totally undetectable, even upon histological examination of the former tumor bearing region.

Response to a given attenuated measles virus dose was dependent on tumor size. While all of the MVlacZ-injected tumors demonstrated considerable slowing of growth compared to controls, there were substantial differences in the magnitude of response between different sizes of Raji tumors. The mean tumor size of Raji tumors injected with $10^6$ pfu MVlacZ was 0.41 cm$^3$ (range 0.19-0.91) and of tumors injected with 4×10$^7$ pfu MV-Edm was 0.45 cm$^3$ (range 0.21-0.67). There was a significant difference in the response of small (<0.4 cm$^3$) or large (>0.4 cm$^3$) to MV injection as shown in FIG. 2D.

Pathological Effects Related to Measles Virus Infection can be Observed in Injected Tumors Histological sections of tumors which remained after attenuated measles virus therapy were examined and compared with control tumors. Hematoxylin and eosin staining of tumor sections revealed multinucleated giant cells typical of measles virus infection in a proportion of the tumors examined. A measurement of β-galactosidase in these cells are confirmed that tumor regressions observed after measles virus injection are due to the specific cytopathological effects of this virus on tumors cells.

Replicating Measles Virus can be Recovered from Injected Tumors

Figure 3:
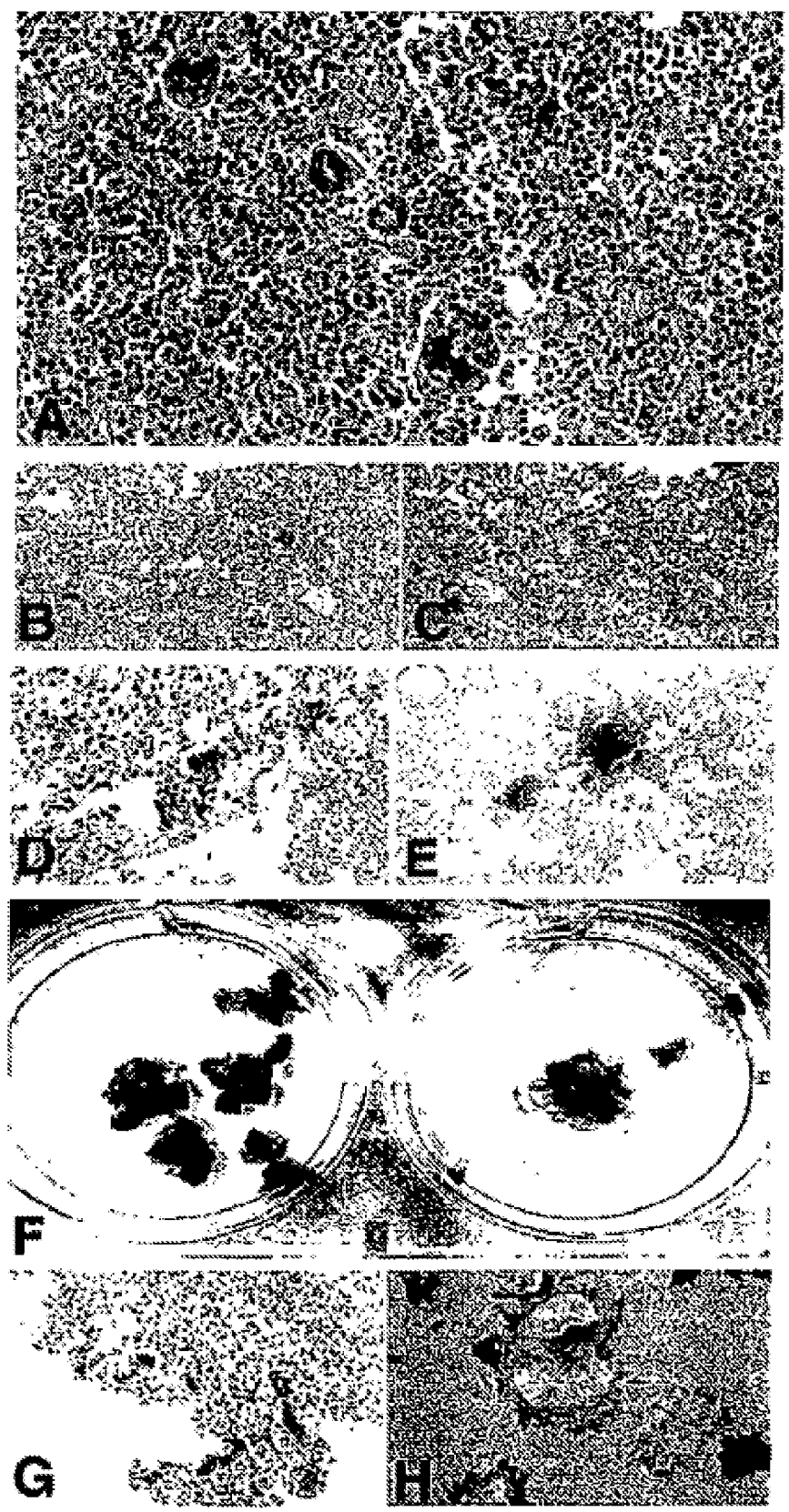
FIGS. 3A-H show cytopathic effects on tumor cells using an attenuated measles virus comprising a marker gene according to one embodiment of the invention and correlation of these effects with expression of the marker gene.

To rule out the possibility that viral replication was compromised under in vitro conditions in some of the tumors, the amount of replicating measles virus, if any, which could be recovered from an injected lesion was determined. A small portion of any tumor remaining at the end of a course of treatment, was excised 20 days after the final injection. The slice was co-cultured with Vero cells for 24 hours. Vero cells were subsequently examined for synctia formation due to the presence of measles virus. Where the injected virus was MVlacZ, it was confirmed that the cytopathic effects seen on Vero cells were confirmed to be due to measles virus rescued from the tumor by X-gal staining. As negative controls, slices of excised non-injected tumors were co-cultured with Vero cells. As assessed by the presence of syncytia on Vero cells, virus was recovered from all attenuated measles virus injected tumors tested. A photomicrograph showing β-galactosidase expression in Vero cells 24 hours after co-culture is shown in FIG. 3G. No syncytia were present after culture with non-injected control tumors.

The titer of residual attenuated measles virus within the tumor 20 days after the final measles virus injection was determined in two Raji tumors. After physical disruption of the tumor, the cells were subjected to two cycles of freeze-thawing and the supernatant was subjected to TCID$_{50}$ determination on Vero cells. The titer of virus recovered from the tumor tissue was similar in both cases, –3.5×10$^5$ and 5×10$^5$ per gram of tumor tissue.

Thus, in this immunodeficient murine model, replication competent attenuated measles virus can be recovered from injected tumors for at least 20 days following injection, indicating that the tumor xenografts are able to sustain in vivo viral replication.

Example 2

Using Attenuated Measles Virus to Limit Growth of Non-Lymphatic Cancers

To test the potency of MV-Edm on cancer cells other than non-Hodgkin lymphoma cells, human melanoma, breast carcinoma, and glioma tumor xenografts were implanted subcutaneously in the hind flank of athymic or SCID mice, in addition to myeloma tumor xenografts. Established tumors were allowed to grow until they reached diameters between 4.3 to 6.4 mm (volume 50-169 mm$^3$). Tumor-bearing mice were treated by intratumoral inoculation of 1×10$^7$ pfu of MV-Edm in 100 μl of Opti-MEM 1 and administered twice a week for a total of seven doses. Control tumors were injected with equivalent amounts of UV-inactivated virus. MV-Edm markedly repressed the growth of all tumors tested and caused regression of the melanoma and myeloma tumors. In keeping with the lymphotropic nature of the measles virus, MV-Edm was found to be most effetive against ARH-77 myeloma xenografts. Tumors were highly sensitive to 10$^7$ pfu of MV-Edm and all treated tumors regressed completely. On ARH-77 tumor re-grew after therapy but regressed completely when injected with an additional single dose of 1×10$^7$ pfu/100 μl of MV-Edm.

Figure 4:
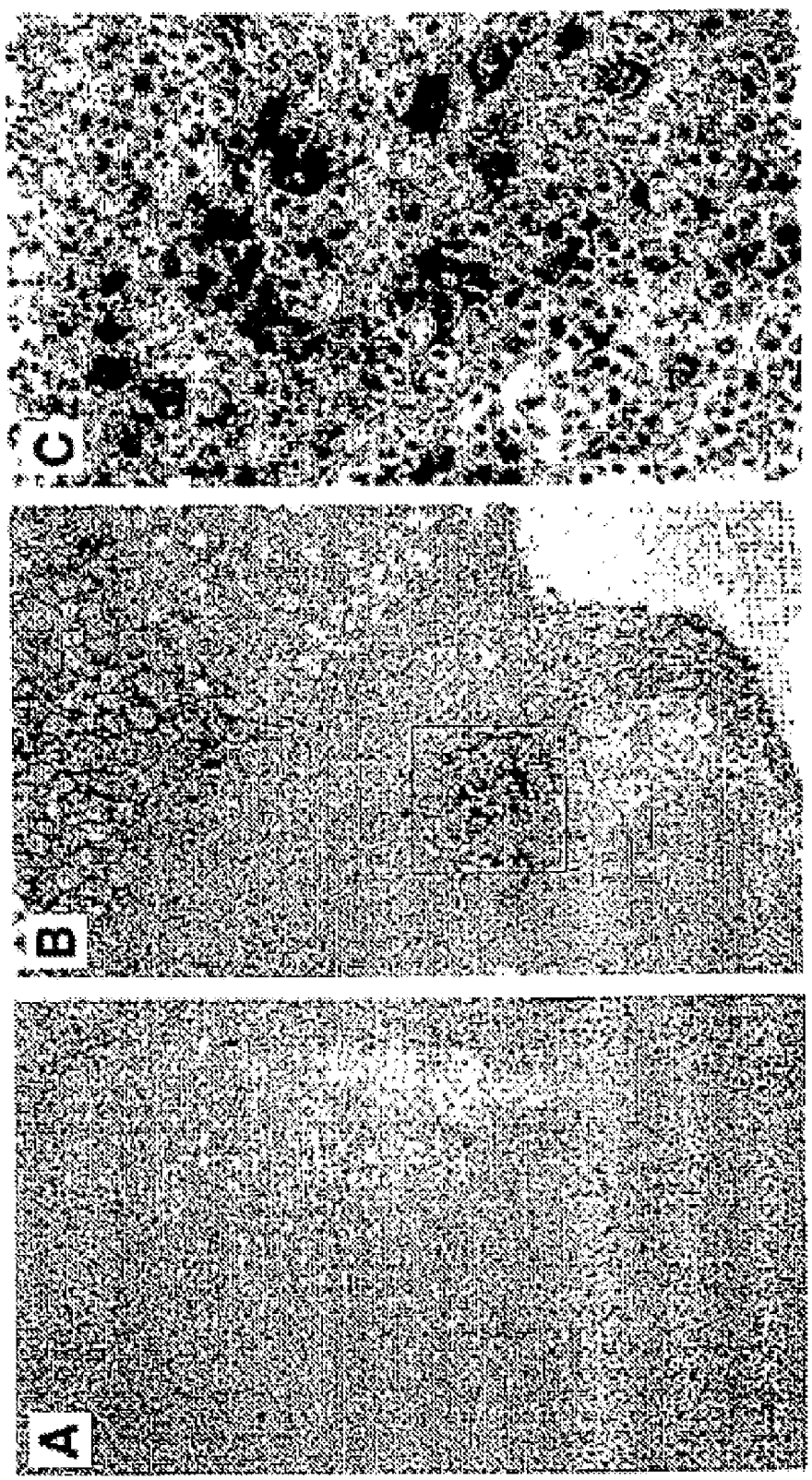
FIGS. 4A-C show expression of measles virus nucleocapsid mRNA (N mRNA) in ARH-77 xenografts from mice who were injected intraumorally with Edmonton strain of attenuated measles virus (MV-Edm).

To detect virus infection and replication, ARH-77 xenografts were injected with 1×10$^7$ pfu MV-Edm or UV inactivated MV and harvested 3 days later. Multinucleated syncytia were observed in hematoxylin and eosin stained sections of tumors inoculated with MV-Edm, but not in control tumors. Analysis of tumor sections by in situ hybridization for measles virus nucleocapsid (N) mRNA confirmed that the syncytia in virus-inoculated tumors contained abundant MV-Edm RNA (see FIGS. 4A-C).

Example 3

Figure 5:
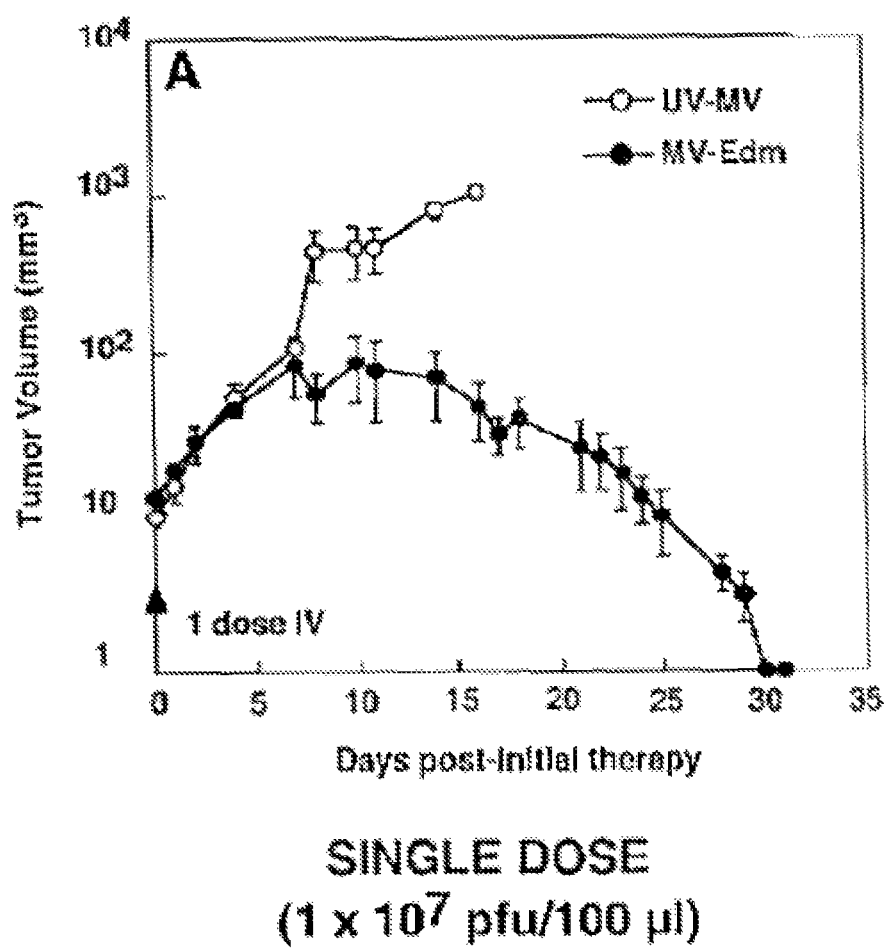
FIGS. 5A-B show regression of subcutaneous ARH-77 myeloma tumor xenografts after intravenous administration of MV-Edm into tumor-bearing animals.
Figure 5:
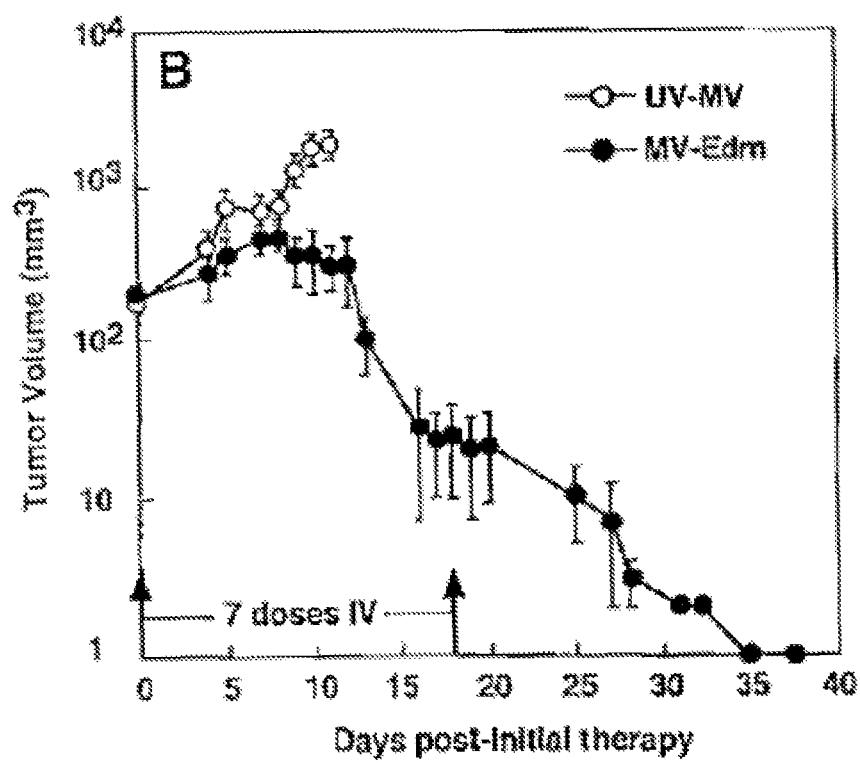

Intravenous Administration of MV-Edm Caused Complete Regression of Myeloma Xenografts For systemic therapy using attenuated measles virus (e.g., to treat disseminated cancer cells), the antineoplastic potential of intravenously injected attenuated measles virus was determined. In one embodiment, SCID mice (CD-46 negative) bearing established ARH-77 meyeloma xenografts (CD46 receptor-positive) were treated by intravenous administration of 1×10$^7$ pfus of MV-Edm in 100 μl Opti-MEM adminstered as a single dose or repeated on alternate days for a total of seven doses (see FIGS. 5A-B). Control tumor-bearing mice were injected with equivalent amounts of UV-inactivated virus. Intravenous administration of a single dose of MV-Edm caused complete regression of 12 mm$^3$ tumors in all treated animals by repeated intravenous administration of the same does MV-Edm (FIG. 6B). No treatment-related toxicity was observed, even at highest doses of MV-Edm, and treated animals remained in good health for the duration of the experiment. No anti-tumor effect was seen post-treatment with UV inactivated virus.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A method of treating cancer, wherein said method comprises:
   (a) administering a therapeutically effective dose of attenuated measles virus to a patient so as to reduce the number of cancer cells in the patient, wherein said cancer cells are part of a tumor, and
   (b) monitoring a reduction of the size of said tumor.

2. The method of claim 1, wherein said attenuated measles virus is injected directly into said tumor.

3. The method of claim 2, wherein said attenuated measles virus is provided in a formulation comprising an excipient.

4. The method of claim 3, wherein said attenuated measles virus formulation is provided continuously to said patient.

5. The method of claim 3, wherein said attenuated measles virus formulation is provided in pulses to said patient.

6. The method of claim 1, wherein said attenuated measles virus is administered systemically to said patient.

7. The method of claim 1, wherein said attenuated measles virus is administered at a dose greater than about 10$^3$ pfu.

8. The method of claim 7, wherein said dose is about 10$^5$ pfus.

9. The method of claim 7, wherein said dose is about 10$^6$ pfus.

10. The method of claim 7, wherein said dose is about 10$^7$ pfus.

11. The method of claim 7, wherein said dose is about 10$^8$ pfus.

12. The method of claim 1, wherein said attenuated measles virus is provided in a composition further comprising attenuated mumps virus and attenuated rubella virus.

13. The method of claim 1, wherein said attenuated measles virus is provided in a composition further comprising attenuated rubella virus.

14. The method of claim 1, wherein said attenuated measles virus is genetically modified to express a marker polypeptide, and wherein expression of said marker polypeptide correlates with replication of said attenuated measles virus.

15. The method of claim 14, wherein said marker polypeptide is β-galactosidase or Green Fluorescent Protein.

16. The method of claim 1, wherein said cancer cells are selected from the group consisting of melanoma cells, carcinoma cells, glioma cells, and myeloma cells.

17. The method of claim 16, wherein said cancer cells are myeloma cells.

18. The method of claim 16, wherein said cancer cells are Non-Hodgkin's Lymphoma cells.

19. The method of claim 1, wherein said attenuated measles virus is provided within a vaccine formulation.

20. The method of claim 19, wherein said vaccine is the MMR-II vaccine.

21. The method of claim 1, wherein said attenuated measles virus is selected from the group consisting of the Edmonston Zagreb measles strain, the Edmonston-Enders strain, the Moraten strain, and the Moraten Berna strain.

22. The method of claim 1, wherein said attenuated measles virus comprises a strain obtained after serial passage of either the Moraten strain or the Moraten Berna strain on non-human cells.

23. The method of claim 1, wherein said attenuated measles virus comprises a strain obtained after serial passage of the Edmonston strain, the Edmonston Zagreb strain, or the Edmonston Enders strain on non-human cells.

* * * * *